United States Patent [19]

Takai et al.

[11] Patent Number: 4,668,683
[45] Date of Patent: May 26, 1987

[54] CARDIOTONIC QUINAZOLINE DERIVATIVES

[75] Inventors: Haruki Takai; Yuji Nomoto, both of Shizuoka; Tadashi Hirata, Kanagawa; Tetsuji Ohno; Kazuhiro Kubo, both of Shizuoka, all of Japan

[73] Assignee: Kyowa Hakko Kogyo K.K., Tokyo, Japan

[21] Appl. No.: 841,656

[22] Filed: Mar. 20, 1986

[30] Foreign Application Priority Data

Mar. 20, 1985 [JP] Japan ................... 60-57474

[51] Int. Cl.[4] ................ A61K 31/505; C07D 401/14; C07D 403/14
[52] U.S. Cl. ................................... 514/259; 544/293
[58] Field of Search ...................... 544/293; 514/259

[56] References Cited

U.S. PATENT DOCUMENTS 4,188,391  2/1980  Campbell et al. .............. 544/293
4,489,075 12/1984  Campbell et al. .............. 544/293
4,542,132  9/1985  Campbell et al. .............. 544/293

Primary Examiner—Glennon H. Hollrah
Assistant Examiner—James H. Turnipseed
Attorney, Agent, or Firm—Wolder, Gross & Yavner

[57] ABSTRACT

Quinazoline derivatives and their pharmaceutically acceptable acid addition salts having the general formula

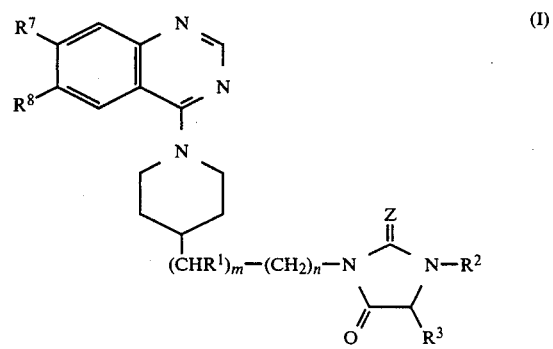

wherein
$R^1$ and $R^2$ each represents hydrogen or alkyl;
$R^3$ represents alkyl or substituted alkyl;
$R^7$ and $R^8$ each represent alkoxy;
Z is oxygen or sulfur;
m is zero or 1;
n is zero or an integer from 1 to 5, exhibit a cardiotonic activity with little tendency to cause tachycardia.

7 Claims, No Drawings

CARDIOTONIC QUINAZOLINE DERIVATIVES

The present invention relates to quinazoline derivatives and pharmaceutically acceptable acid addition salts thereof, having a cardiotonic activity.

It is known that quinazoline derivatives of the following formula exhibit a cardiotonic activity (U.S. Pat. No. 4,001,422):

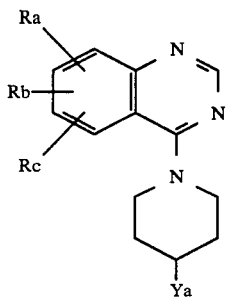

wherein Ra, Rb and Rc each represents a hydrogen atom, a hydroxy group or a lower alkoxy group; among Ra, Rb and Rc, an adjacent two may be combined together to form a methylenedioxy group or an ethylenedioxy group; Ya represents, for example, one of the following formulae:

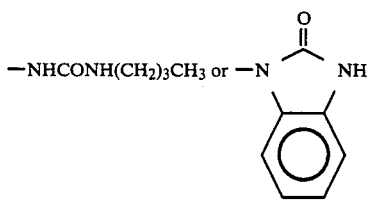

It is also known that quinazoline derivatives represented by the following formula exhibit a cardiotonic activity (U.S. Pat. No. 4,188,391):

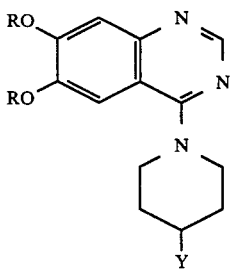

wherein
R represents a lower alkyl group; Y represents a group of the formula:

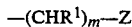

$-(CHR^1)_m-Z$

[wherein $R^1$ represents a hydrogen atom or a lower alkyl group; m represents an integer of 1 or 2; in the case m=2, all of $R^1$ may be the same or different; and Z represents $-OCONR^4R^5$, $-N(R^2)COR^3$, $-N(R^2)SO_2R^3$, or $-N(R^2)CONR^4R^5$
(wherein $R^2$ represents a hydrogen atom or a lower alkyl group; $R^3$ represents a lower alkyl group, a benzyl group or a phenyl group; $R^4$ and $R^5$ are independent and each represents a hydrogen atom or a group as hereinbefore defined for $R^3$)].

It is further known that quinazoline derivatives represented by the following formula exhibit a cardiotonic activity (U.S. Pat. No. 4,489,075):

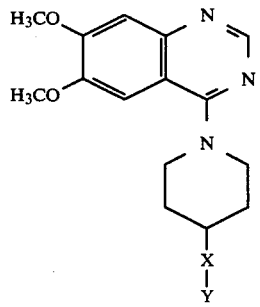

[wherein X represents a straight or branched alkyl group having 1–4 carbon atoms; and Y represents one of the following formulae:

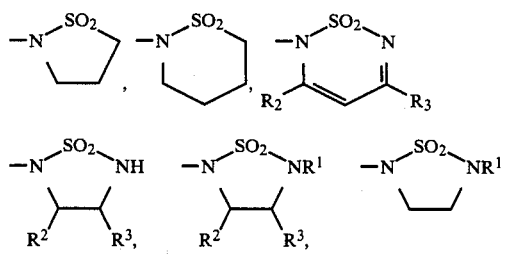

(wherein $R^1$ represents hydrogen or an alkyl group having 1–4 carbon atoms; $R^2$ and $R^3$ are independently hydrogen or $CH_3$)].

However, the quinazoline derivatives of the present invention differ substantially from the known compounds by containing as a novel structural feature a hydantoin or thiohydantoin ring.

In one aspect, our invention provides quinazoline derivatives and pharmaceutically acceptable acid addition salts thereof having the general formula

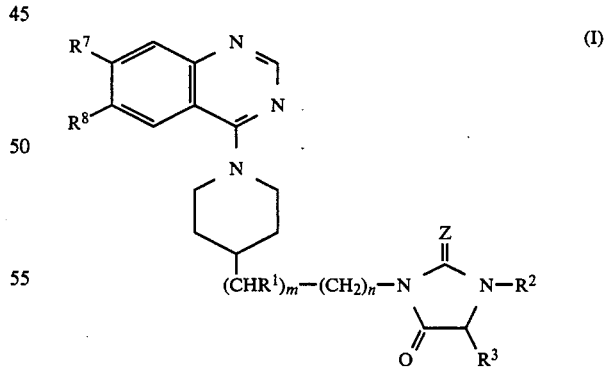

[wherein $R^1$ and $R^2$ each represents hydrogen or alkyl;
$R^3$ represents alkyl or a group of the formula: $-(CH_2)_p-Q$; or
$R^2$ and $R^3$ may together form the group $-CH_2CH_2CH_2-$;
Q represents hydroxy, alkylthio, imidazolyl or optionally substituted phenyl;
p represents an integer of from 1 to 5;

$R^7$ and $R^8$ each represents alkoxy;

Z represents an oxygen or sulfur atom;

m represents 0 or 1; and n represents 0 or an integer of from 1 to 4.

The compounds of our invention have been found to exhibit a long-lasting cardiotonic activity. Unlike some other cardiotonic agents, our compounds have little tendency to cause excessive or dangerous tachycardia.

In the definition of $R^2$ and $R^3$ of the general formula (I), the alkyl groups may e.g. be straight or branched alkyl groups containing 1–6 carbon atoms such as, for example, methyl, ethyl, n-propyl, iso-propyl, n-butyl, sec-butyl, tert-butyl, n-pentyl, sec-pentyl, n-hexyl and sec-hexyl groups.

The alkylthio groups in the definition of $R^3$ include, for example, alkylthio groups containing 1–5 carbon atoms such as, for example, a methylthio group.

In the definition of $R^7$ and $R^8$, the alkoxy groups may e.g. contain 1–5 carbon atoms such as, for example, methoxy and ethoxy groups.

The substituents of the optionally substituted phenyl group are exemplified by a hydroxy, methoxy, ethoxy and benzyloxy.

With respect to pharmaceutically acceptable acid addition salts of Compounds I, various inorganic acid salts such as, for example, the hydrochloride, hydrobromide, hydroiodide, nitrate, sulfate and phosphate may be used or organic acid salts such as, for example, the formate, acetate, acetate, benzoate, malate, fumarate, succinate, tartrate, citrate, oxalate, glyoxylate, aspartate, methanesulfonate, ethanesulfonate, propanesulfonate, methanedisulfonate, $\alpha,\beta$-ethanedisulfonate and benzenesulfonate may be used.

Our invention further provides a number of processes for preparing the compounds (I). Those compounds wherein Z is sulfur, i.e. compounds of the formula:

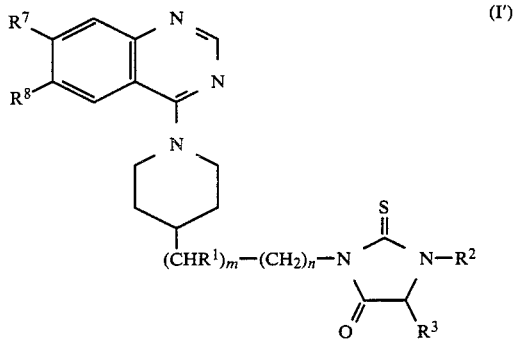

(I')

(wherein $R^1$, $R^2$, $R^3$, $R^7$, $R^8$, m and n are as hereinbefore defined for compounds of formula I) may be prepared by the following methods A and B:

Method A:

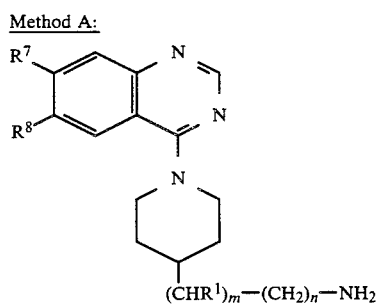

Method A:

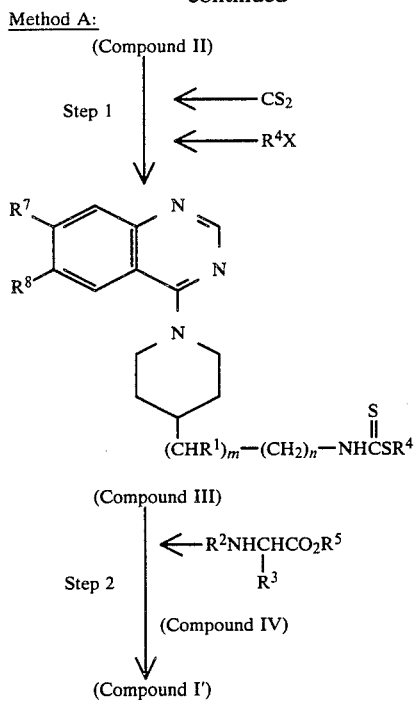

In the above-mentioned formulae, $R^1$, $R^2$, $R^3$, $R^7$, $R^8$, m and n are as hereinbefore defined; $R^4$ represents an alkyl group; $R^5$ represents a hydrogen atom or an alkyl group; X represents a halogen atom; and the alkyl groups may contain 1–5 carbon atoms and are exemplified by methyl or ethyl. The halogen atoms are exemplified by chlorine, bromine and iodine.

The compounds which may be used as starting materials, viz. Compounds (II), are known compounds, disclosed in U.S. Pat. No. 4,188,391 and U.S. Pat. No. 4,001,422.

Preferred procedures for effecting each step are as follows:

Step 1

The reaction of Compound (II) with carbon disulfide is effected in the presence of an inert solvent optionally in the presence of a base, followed by reaction with an alkyl halide to obtain compound (II). As compound (II), 4-amino-1-(6,7-dimethoxyquinazolin-4-yl)piperidine, 4-aminomethyl-1-(6,7-dimethoxyquinazolin-4-yl)piperidine, 4-(2-aminoethyl)-1-(6,7-dimethoxyquinazolin-4-yl)piperidine, 4-(1-aminoethyl)-1-(6,7-dimethoxyquinazolin-4-yl)piperidine, and the like may e.g. be used.

Preferred inert solvents for this reaction include, for example, lower alcohols such as methanol, ethanol and isopropanol; halogenated hydrocarbons such as chloroform and methylene chloride; amides such as dimethylformamide; and sulfoxides such as dimethylsulfoxide. These solvents may be used alone or in admixture. The bases which may be used are exemplified by tertiary amines such as triethylamine and pyridine; alkali metal carbonates such as sodium carbonate and potassium carbonate, and the like.

The reaction is carried out, for example, for 1–4 hours at 0°–40° C., preferably at room temperature after addition of carbon disulfide. Subsequently, a further reaction may be effected, for example, for 0.5–2 hours at 0°–40° C., preferably at room temperature, after addition of alkyl halide.

Step 2

The reaction of Compound (III) and Compound (IV) may be effected in the presence of an inert solvent optionally in the presence of a base to obtain Compound (I′). Compound (IV) is a known compound and exemplified by an amino acid (L, D or D,L-form) or an alkyl ester containing 1-3 carbon atoms such as, for example, alanine, norvaline, leucine, methionine, phenylglycine, homoserine, phenylalanine, histidine, valine, isoleucine, glycine, norleucine, proline, N-methyl-glycine, N-methyl-valine; N-methyl-isoleucine, methyl N-methyl-L-valate, and ethyl N-methyl-L-valate. The inert solvents mentioned in step 1 may be used in this step. The bases which may be used include, for example, tertiary amines such as triethylamine and pyridine, alkali metal carbonates such as sodium carbonate and potassium carbonate, and the like.

The amount of the base used may be, for example, 1.0–2.0 equivalents calculated on the basis of compound (IV) when $R^5$ is a hydrogen atom and 0–1.0 equivalent when $R^5$ is an alkyl group. When the Compound (IV) is used as its acid addition salt such as the hydrochloride, an additional amount of the base is of course required for neutralizing the acid.

Usually, the reaction may be continued, for example, for 5–20 hours at 60°–100° C., preferably with heating at the boiling point of the solvent employed.

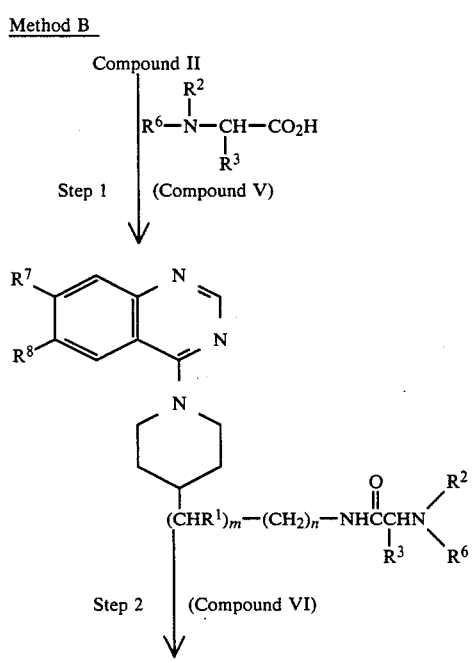

Method B
Compound II

Step 1 (Compound V)

Step 2 (Compound VI)

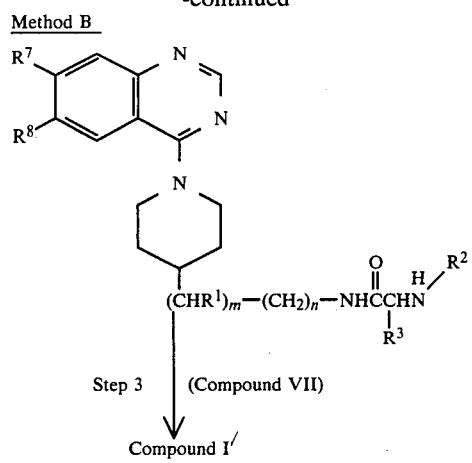

Method B -continued

Step 3 (Compound VII)

Compound I′

In the formulae, $R^1$, $R^2$, $R^3$, $R^7$, $R^8$, m and n are as hereinbefore defined for compounds of formula I; and $R^6$ represents a protecting group for an amino group such as, for example a benzyloxycarbonyl or a tert-butoxycarbonyl group.

Preferred procedures for effecting each step are described in detail as follows:

Step 1

Compounds (II) and (V) are condensed to obtain Compound (VI). Compound (V) is a known compound and exemplified by N-protected amino acids (L, D or D,L-form) such as N-tert-butoxycarbonyl amino acids e.g. N-tert-butoxycarbonyl-valine (hereinafter referred to as Boc-valine), Boc-phenylalanine, Boc-alanine, Boc-methionine, Boc-O-benzyl-tyrosine, Boc-leucine, Boc-glycine, Boc-isoleucine, Boc-proline, Boc-serine, Boc-N-methyl-glycine, etc., and by N-benzyloxycarbonyl amino acids (L, D or D,L-form) e.g. N-benzyloxycarbonyl-alanine (hereinafter referred to as N-CBZ-alanine), N-CBZ-S-benzyl-cysteine, N-CBZ-O-benzyl-serine, N-CBZ-O-benzyl-threonine, N-CBZ-O-benzyl-tyrosine, N-CBZ-glycine, N-CBZ-methionine, N-CBZ-norleucine, N-CBZ-norvaline, N-CBZ-phenylalanine, N-CBZ-proline, N-CBZ-serine, N-CBZ-threonine, N-CBZ-valine, N-CBZ-tyrosine. Condensing agents which may be used to assist the reaction are exemplified by those conventionally used for peptide synthesis such as N,N′-dicyclohexylcarbodiimide, alkyl chlorocarbonate and the like. The reaction may be effected usually for 1–2 hours at 0° C. to −20° C. and then for 1–24 hours at room temperature.

Step 2

Compound (VII) may be obtained by removing the protecting group $R^6$ from Compound (VI). For this purpose, various deprotecting methods conventionally used in peptide synthesis may be selected having regard to the nature of the protecting group $R^6$.

Step 3

Reaction of compouned (VII) with carbon disulfide, thiophosgene, N,N′-thiocarbonyldiimidazole and the like may be effected in an inert solvent in the presence of a base to obtain Compound (I′).

The inert solvents which may be used for this purpose are exemplified by lower alcohols such as methanol, ethanol and isopropanol; halogenated hydrocarbons such as chloroform and methylene chloride; amides such as dimethylformamide; sulfoxides such as dimethylsulfoxide and the like; such solvents may be used alone or in admixture. The bases which may be used are exemplified by tertiary amines such as triethylamine and pyridine, alkali metal carbonates such as sodium carbonate and potassium carbonate; alkali metal hydroxides such as sodium hydroxide, and the like. The amount of the base used may e.g. be 1.0–2.0 equivalents based on the amount of Compound (VII). Where Compound (VII) is used as its acid addition salt, such as the hydrochloride, an additional amount of the base is of course required for neutralizing the acid.

Usually the reaction may be effected for 30 minutes to 24 hours at 60°–100° C.

Those Compounds (I) wherein Z is oxygen, i.e. compounds of formula

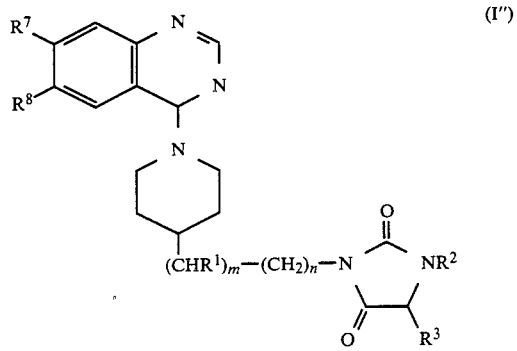

(I'')

[wherein $R^1$, $R^2$, $R^3$, $R^7$, $R^8$, m and n are as hereinbefore defined for compounds of formula I], may be prepared by reacting Compounds (VII) with a suitable carbonyl derivative, e.g. a carbonyl halide such as phosgene, in alkyl halo-, preferably chloro-carbonate, a diester of carbonic acid, 1,1-carbonyldiimidazole, or other chemically equivalent reagent.

The above-mentioned reaction may be carried out in a conventional manner, but a reaction using 1,1'-carbonyldiimidazole is exemplified as follows:

The reaction may be effected in aprotic polar solvents such as halogenated hydrocarbons (e.g. methylene chloride and ethylene chloride), ethers (e.g. ethylether, tetrahydrofuran, dioxane, acetonitrile, dimethylformamide, dimethylsulfoxide and the like), which solvents may be used alone or in admixture, preferably while stirring. In some cases, depending upon the nature of the starting material viz. Compound (VII), the reaction may be advantageously effected in the presence of a base. The bases which may be used for this purpose are exemplified by 1,8-diazabicyclo[5,4,0]undec-7-ene, trimethylamine and the like.

The reaction may be effected, for example, for 1–3 hours at the boiling point of the selected solvent or for 8–12 hours at room temperature.

Isolation and purification of Compounds (I) (viz. Compounds (I') and (I'')) as well as the above-mentioned intermediates may be effected by methods conventionally used in organic synthesis, such as evaporation, extraction, chromatography and the like.

Pharmaceutically acceptable acid addition salts of Compounds (I) may be obtained by reacting a Compound (I) with suitable acid in a suitable solvent (e.g. ethanol), preferred acids being exemplified by hydrochloric acid, hydrobromic acid, hydroiodic acid, nitric acid, sulfuric acid, phosphoric acid, formic acid, acetic acid, benzoic acid, maleic acid, fumaric acid, succinic acid, tartaric acid, citric acid, oxalic acid, glyoxylic acid, aspartic acid, methanesulfonic acid, ethanesulfonic acid, propanesulfonic acid, methanedisulfonic acid, α,β-ethanedisulfonic acid, benzenesulfonic acid and the like.

The cardiotonic Compounds (I) and/or pharmaceutically acceptable acid addition salts thereof may be formulated into pharmaceutical compositions comprising a physiologically acceptable carrier, excipient and/or adjuvant. Such compositions may take suitable forms conventionally used in the art of pharmacy such as, for example, tablets, capsules, syrups, injectable compositions, drips, suppositories and the like. The administration thereof may be effected, for example, by oral administration, injection (intramuscular, intravenous, intraarterial), parenteral drip, rectal administration (suppositories) and other extrabuccal routes. Compositions for such oral and extrabuccal administrations may be prepared in conventional manner used in the art and may contain, for example, various excipients, lubricants, binders, disintegrators, dispersants, isotonizating agents, emulsifiers and the like.

Preferred carriers for this purpose are exemplified by water, distilled water for injection, physiological saline, glucose, fructose, sucrose, mannitol, lactose, starch, cellulose, methylcellulose, carboxymethylcellulose, hydroxypropylcellulose, alginic acid, talc, sodium citrate, calcium carbonate, dibasic calcium phosphate, magnesium stearate, urea, silicone resin, sorbitan fatty acid ester, glycerol fatty acid ester and the like.

The compositions may be orally administered at a rate to give a dosage of active ingredient of, for example, 5–200 mg/60 kg body weight; in the case of infusion, it is possible to administer, for example, 0.1–5 mcg/kg/body weight/min of active ingredient although the total amount should not be greater than the maximum dose for oral administration.

The following Examples illustrate the invention, in which R in the formulae represents the group

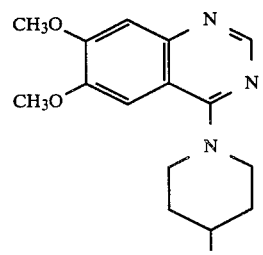

EXAMPLE 1

Preparation of 1-(6,7-dimethoxyquinazolin-4-yl)-4-(5-isopropyl-4-oxo-2-thioxoimidazolidin-3-yl)methyl piperidine:

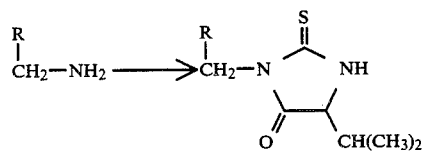

A mixture of 6,7-dimethoxy-4-[4-(aminomethyl)-piperidino] quinazoline (302 mg; 1 mmol), triethylamine (0.14 ml; 1 mmol), carbon disulfide (66 mcl; 1 mmol) and ethanol (3 ml) was stirred at room temperature for 2 hours. After addition of methyl iodide (62 mcl; 1 mmol), the mixture was further stirred for 1 hour. After addition of L-valine (351 mg; 3 mmol) and triethylamine (0.42 ml, 3 mmol), the reaction solution was refluxed for 10 hours. The resultant reaction solution was left at room temperature for 12 hours to precipitate crystals which were then recovered by filtration. The crystals were successively washed with an aqueous solution of 10% NaHCO₃, water and ethanol and dried. The dried material was recrystallized by using a mixture of chloroform and ethanol to yield the desired product (188.6 mg; 41.1%).

EXAMPLES 2-10

In each instance, a similar procedure to that described in Example 1 was effected except that the amino acids as shown in Table 1 were used instead of L-valine, to obtain the desired products (Compounds 2-10).

TABLE 1

| Example | Amino acid | Yield (%) |
|---|---|---|
| 2 | Methyl N—methyl-L-valate | 84.5 |
| 3 | D,L-alanine | 16.5 |
| 4 | D,L-norvaline | 43.3 |
| 5 | D,L-leucine | 29.3 |
| 6 | L-methionine | 9.8 |
| 7 | D,L-phenylglycine | 25.1 |
| 8 | L-homoserine | 52.4 |
| 9 | L-phenylalanine | 45.5 |
| 10 | L-histidine | 27.0 |

EXAMPLE 11

Preparation of 1-(6,7-dimethoxyquinazolin-4-yl)-4-(5-isopropyl-4-oxo-2-thioxoimidazolidin-3-yl)piperidine:

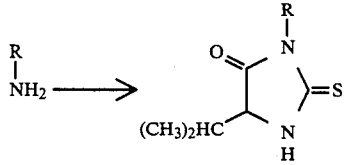

4-Amino-1-(6,7-dimethoxyquinazolin-4-yl)piperidine (0.9 g) was added to a mixture of Boc-L-valine (1.3 g), N,N'-dicyclohexylcarbodiimide (0.7 g) and acetonitrile (30 ml) while cooling with ice. The mixture was further stirred at room temperature for 30 minutes. Insoluble substances were removed from the reaction solution by filtration. The filtrate was concentrated and partitioned between ethyl acetate and a saturated aqueous solution of NaHCO₃. The organic layer was dried over anhydrous magnesium sulfate and concentrated. By purification using a 40 g silica gel column, 4(Boc-L-valyl-)amino-1-(6,7-dimethoxyquinazolin-4-yl)piperidine (1 g, 74%) was obtained.

The resulting material (0.8 g) was dissolved in methanol (5 ml). To the solution was added an ethyl acetate solution saturated with hydrogen chloride (1 ml). The mixture was stirred for 12 hours to precipitate crystals which were recovered by filtration. The crystals were washed with ethyl acetate and dried to obtain 4-(L-valyl) amino-1-(6,7-dimethoxyquinazolin-4-yl)piperidine (2HCl; 0.9 g; 80%).

A mixture of the resulting product (0.4 g), ethanol (9 ml), carbon disulfide (0.9 ml) and triethylamine (0.4 ml) was stirred for 6 hours under reflux. The reaction mixture was cooled and concentrated to precipitate crystals. The separated crystals were suspended in water and recovered by filtration. The recovered material was dissolved in chloroform and was then purified by using a 40 g silica gel column to yield the desired product (0.1 g; 16%).

EXAMPLES 12-14

In each instance, a similar procedure to that described in Example 11 was effected except that the protected amino acid shown in Table 2 was used instead of Boc-L-valine to obtain the yield of products (Compounds 12-14) shown in Table 2.

TABLE 2

| Example | Protected amino acid | Yield (%) |
|---|---|---|
| 12 | Boc—L-phenylalanine | 67.0 |
| 13 | Boc—L-alanine | 28.0 |
| 14 | Boc—L-methionine | 6.0 |

EXAMPLE 15

Preparation of 1-(6,7-dimethoxyquinazolin-4-yl)-4-(5-isopropyl-2,4-dioxoimidazolidin-3-yl)methylpiperidine:

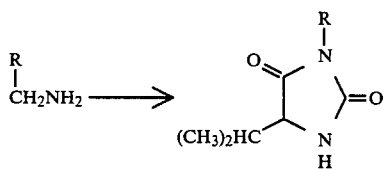

Isobutyl chlorocarbonate (0.4 ml; 3 mmol) was added to a mixture of Boc-L-valine (651.8 mg; 3 mmol), N-methyl-morpholine (303.5 mg; 3 mmol) and tetrahydrofuran (20 ml) while stirring. After 10 minutes, a DMF solution (10 ml) containing 6,7-dimethoxy-4-[4-(aminomethyl)piperidino]quinazoline (906 mg; 3 mmol) was added to the reaction solution at a temperature of not higher than 0° C. The reaction solution was then stirred at −5° C. for 1 hour and concentrated under reduced pressure. To the resulting residue was added chloroform (100 ml), and the mixture was washed with an aqueous solution of 10% NaHCO₃ and water, dried and concentrated under reduced pressure to give 1-(6,7-dimethylquinazolin-4-yl)-4-[2-(Boc-L-valyl)]aminomethylpiperidine as an oil.

To the resulting material was added a solution of 1.7N HCl and ethyl acetate (150 ml), and the mixture was stirred for 12 hours at room temperature. The precipitated insoluble material was recovered by filtration to give 1-(6,7-dimethoxyquinazolin-4-yl)-4-(L-valyl-)aminomethyl piperidine.2HCl. The resulting material was suspended in acetonitrile (90 ml). To this suspension was added triethylamine (0.96 ml; 6.9 mmol). Then, N,N'-carbonyldiimidazole (1.5 g; 9.3 mmol) was added to the mixture while stirring at room temperature. The reaction mixture was stirred at room temperature for 6 hours and concentrated to give an oil. The oil was dissolved in chloroform (90 ml) and the solution was washed with water, dried and concentrated under reduced pressure to give an oily material which was subjected to chromatography on silica gel with elution in mixture of CH₂Cl₂ and MeOH (40:1 v/v) to yield the desired product (309 mg; 24.1%).

EXAMPLES 16-20

A similar procedure to that described in Example 15 was effected by using, in each instance, the protected amino acid shown in Table 3 instead of Boc-L-valine to obtain the yields of desired products (Compounds 16-20) as shown in Table 3.

TABLE 3

| Example | Protected amino acid | Yield (%) |
|---|---|---|
| 16 | Boc—L-phenylalanine | 22.5 |
| 17 | Boc—O—benzyl-L-tyrosine | 6.7 |
| 18 | Boc—L-leucine | 31.0 |
| 19 | Boc—L-methionine | 11.9 |
| 20 | Boc—glycine | 15.3 |

EXAMPLE 21

Preparation of 1-(6,7-dimethoxyquinazolin-4-yl)-4-(5-isopropyl-2,4-dioxoimidazolidin-3-yl)piperidine:

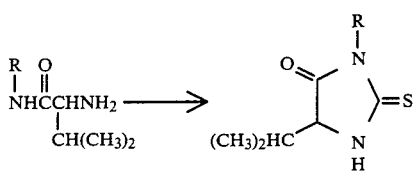

4-(L-valyl)amino-1-(6,7-dimethoxyquinazolin-4-yl)piperidine.2HCl (0.4 g) prepared by the method of Example 11 was suspended in acetonitrile (10 ml). To the suspension was added triethylamine (0.4 ml) and N,N'-carbonyldiimidazole (0.3 g) and the mixture was stirred at 50° C. for 2 hours. The reaction solution was concentrated and partitioned between chloroform and water. The chloroform layer was dried over anhydrous magnesium sulfate and concentrated. The residue was purified by using a 40 g silica gel column to yield the desired product (0.1 g; 15%).

EXAMPLES 22–23

The procedure described in Example 21 was repeated except that the starting material shown in Table 4 was used instead of 4-L-valyl)amino1-(6,7-dimethoxyquinazolin-4-yl)piperidine. The yields are shown in Table 4.

TABLE 4

| Example | Starting material | Yield (%) |
|---|---|---|
| 22 | 4-(L-methionyl) amino-1-(6,7-dimethoxyquinazolin-4-yl) piperidine | 39.0 |
| 23 | 4-(L-phenylalanyl) amino-1-(6,7-dimethoxyquinazolin-4-yl) piperidine | 77.0 |

EXAMPLE 24

Preparation of 1-(6,7-dimethoxyquinazolin-4-yl)-4-{2-(1,3-diazabicyclo[3.3.0]oct-2,4-dioxo-3-yl)ethyl}piperidine:

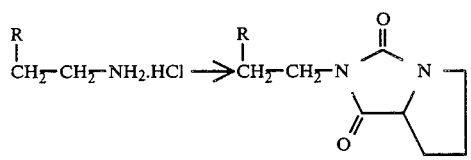

N,N'-dicyclohexylcarbodiimide (0.53 g) was added to a mixture of 4-(2-aminoethyl)-1-(6,7-dimethoxyquinazolin-4-yl)piperidine.2HCl (1.2 g), Boc-L-proline (1.1 g), triethylamine (0.72 ml) and acetonitrile (20 ml). The mixture was stirred at room temperature for 12 hours and filtered. The filtrate was dried and concentrated under reduced pressure. The residue was partitioned between an aqueous solution of 10% NaHCO$_3$ and chloroform. The organic layer was dried over anhydrous magnesium sulfate, concentrated and purified by using a 40 g silica gel column to give 4-{2-(Boc-L-prolylamino)ethyl}-1-(6,7-dimethoxyquinazolin-4-yl)piperidine (1.23 g; 93%).

The resulting material (1.2 g) was dissolved in trifluoroacetic acid (4 ml). After stirring for 30 minutes, water (50 ml) was added thereto. Then a saturated aqueous solution of NaHCO$_3$ was added thereto to give an alkaline pH. After addition of chloroform, the solution was partitioned. The resulting organic layer was dried over anhydrous magnesium sulfate, concentrated and purified by using a 100 g silica gel column to give 4-{2-(L-prolylamino)ethyl}-1-(6,7-dimethoxyquinazolin-4-yl)piperidine (0.77 g; 81%). A mixture of the resulting material (0.3 g), acetonitrile (20 ml), 1,8-diazabicyclo[5.4.0]undec-7-ene (0.21 ml) and N,N'-carbonyldiimidazole (0.47 g) was stirred at room temperature for 2 hours. The mixture was concentrated and purified by using a 20 g silica gel colum to yield the desired product (0.1 g; 31%).

EXAMPLE 25

Preparation of 1-(6,7-dimethoxyquinazolin-4-yl)-4-{1-(1,3-diazabicyclo[3.3.0]oct-2,4-dioxo-3-yl)ethyl}piperidine:

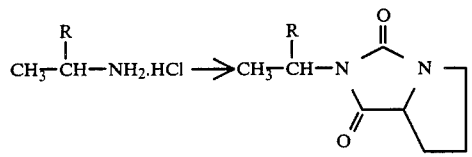

A similar procedure to that described in Example 24 was carried out except that 4-(1-aminoethyl)-1-(6,7-dimethoxyquinazolin-4-yl)piperidine.2HCl was used instead of 4-(2-aminoethyl)-1-(6,7-dimethoxyquinazolin-4-yl)piperidine.2HCl to give the desired product in 30.0% yield.

EXAMPLE 26

Preparation of 1-(6,7-dimethoxyquinazolin-4-yl)-4-{2-(5-isopropyl-2-thio-4-oxoimidazolidin-3yl)ethyl}piperidine:

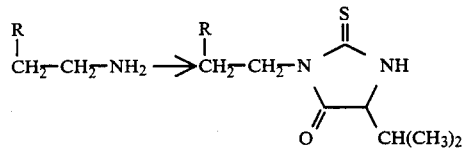

4-(2-aminoethyl)-1-(6,7-dimethoxyquinazolin-4-yl)piperidine (0.1 g) and N-methylthiocarbonyl-L-valine methylester (0.8 g) were dissolved in dimethylformamide (10 ml), and the mixture was stirred at 120° C. for 6 hours. The reaction solution was concentrated to obtain a residue. Chloroform and water were added to the residue for partition. The organic layer was dried over anhydrous magnesium sulfate and concentrated.

13

The residue was purified by using a 10 g silica gel column to yield the desired product (0.1 g; 41%).

EXAMPLE 27

Preparation of 1-(6,7-dimethoxyquinazolin-4-yl)-4-{2-(5-isopropyl-2,4-dioxoimidazolidin-3-yl)ethyl}piperidine:

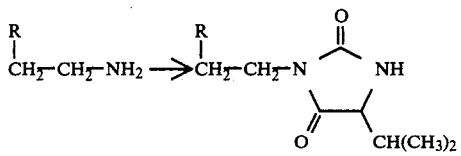

A similar procedure to that described in Example 24 was effected except that Boc-L-valine instead of Boc-L-proline was used to give 4-{2-(L-valylamino)ethyl}-1-(6,7-dimethoxyquinazolin-4-yl)piperidine as intermediate product. Then, 0.3 g of the resulting compound was mixed with acetonitrile (20 ml), 1,8-diazabicyclo[5.4.0]undec-7-ene (0.21 ml) and N,N'-carbonyldiimidazole (0.5 g) and stirred at room temperature for 30 minutes. The reaction solution was concentrated and dimethylformamide (10 ml) was added thereto. The mixture was stirred at 120° C. for one hour, concentrated and purified by using a 20 g silica gel column to yield the desired product (0.14 g; 45%).

EXAMPLE 28

Preparation of 1-(6,7-dimethoxyquinazolin-4-yl)-4-{1-(5-isopropyl-2,4-dioxoimidazolidin-3-yl)ethyl}piperidine:

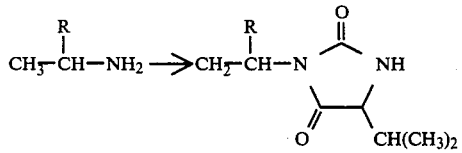

A similar procedure to that described in Example 27 was carried out except that 4-(1-aminoethyl)-1-(6,7-dimethoxyquinazolin-4-yl)piperidine.2HCl was used instead of 4-(2-aminoethyl)-1-(6,7-dimethoxyquinazolin-4-yl)piperidine.2HCl to give the desired product in 14% yield.

14

EXAMPLE 29

Preparation of hydrochloride salt of Compound 1:

Compound 1 (272 mg) was suspended in methanol (5 ml). Then, 5.9N HCl/methanol (4 ml) was added thereto and the compound was dissolved by heating the mixture. The solution was concentration under reduced pressure. The residue was collected and recrystallized from methanol to yield the monohydrochloride salt (188 mg).

Melting point (°C.): 217.0–218.5
IR (KBr; cm$^{-1}$): 2800–2200, 1744
NMR (CDCl$_3$+CD$_3$OD): δ0.96, 1.11, 4.0, 4.1, 4.7–5.0, 7.2, 7.6, 8.6.

EXAMPLE 30

Preparation of hydrochloride salt of Compound 2:

Compound 2 (192 mg) was dissolved in methanol (4 ml). Then, 5.9N HCl/methanol (4 ml) was added thereto, and the solution was concentrated under reduced pressure. The residue was recrystallized from methanol to yield a desired monohydrochloride salt (131 mg).

Melting point (°C.): 156.0–159.0
IR (KBr; cm$^{-1}$: 2800–2200, 1741
NMR (CDCl$_3$): δ0.95, 1.22, 3.4, 4.0, 4.1, 4.6–5.0, 7.2, 8.0 8.6.

EXAMPLE 31

Tablets having the following composition were prepared in conventional manner.

| | |
|---|---|
| Compound 15 | 100 g |
| Magnesium stearate | 4 g |
| Crystalline cellulose | 746 g |

The ingredients are mixed for 5 minutes and then the resulting mixed powder is made into 10,000 tablets of 6.0 mm in diameter, 2.5 mm in thickness, and 85 mg in weight using a tablet-making machine equipped with a pestle having a plane surface and round corners.

The physical characteristics of the products of the above Examples are shown in Table 5 wherein the indicated compound numbers correspond to the Example numbers as hereinbefore described.

TABLE 5

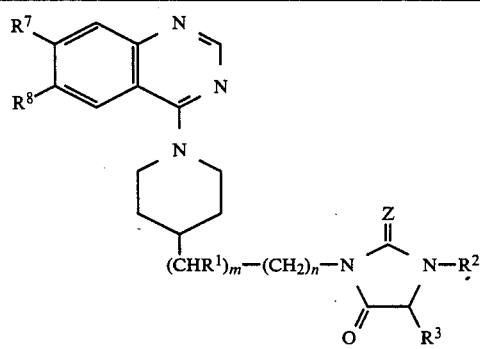

(I)

| No. | Formula (I) | | | | | | | | M.P. | IR(KBr) | NMR(δ) | |
|---|---|---|---|---|---|---|---|---|---|---|---|---|
| | m | n | Z | R$^1$ | R$^2$ | R$^3$ | R$^7$ | R$^8$ | (°C.) | (cm$^{-1}$) | (ppm) | Solvent |
| 1 | 1 | 1 | 0 | S | H | H | CH(CH$_3$)$_2$ | OCH$_3$ | OCH$_3$ | 218.5~220.0 | 1742 1619 1579 | 8.7, 8.0 7.3, 7.1 4.3–0.9 | CDCl$_3$ |

TABLE 5-continued

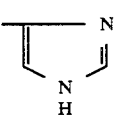

| No. | m | n | Z | R¹ | R² | R³ | R⁷ | R⁸ | M.P. (°C.) | IR(KBr) (cm⁻¹) | NMR(δ) (ppm) | Solvent |
|---|---|---|---|---|---|---|---|---|---|---|---|---|
| 2 | 1 | 0 | S | H | CH₃ | CH(CH₃)₂ | OCH₃ | OCH₃ | amorphous | 1508 1737 1620 1576 1504 | 4.00, 4.03 8.7 7.3, 7.1 4.3–2.8, 3.3 2.5–0.8 | " |
| 3 | 1 | 0 | S | H | H | CH₃ | OCH₃ | OCH₃ | 176.8~179.0 | 1720 1619 1580 1508 | 8.7, 8.1 7.3, 7.1 4.4–3.7 4.03, 4.00 3.3–1.4 | " |
| 4 | 1 | 0 | S | H | H | (CH₂)₂CH₃ | OCH₃ | OCH₃ | amorphous | 1743 1619 1578 1503 | 8.7, 7.4 7.2, 4.4–3.7 3.3–1.2 1.0 | " |
| 5 | 1 | 0 | S | H | H | CH₂CH(CH₃)₂ | OCH₃ | OCH₃ | 200.0~203.5 | 1748 1615 1571 1528 1503 | 10.4, 8.5 7.2, 7.1 4.3–0.8 3.93, 3.90 | DMSO-d₆ |
| 6 | 1 | 0 | S | H | H | (CH₂)₂SCH₃ | OCH₃ | OCH₃ | 199.5~202.0 | 1727 1614 1574 1505 | 8.7, 8.3 7.3, 7.1 4.4–1.0 4.03, 4.00 2.1 | CDCl₃ |
| 7 | 1 | 0 | S | H | H | C₆H₅ | OCH₃ | OCH₃ | 251.0~254.0 | 1740 1617 1575 1504 | 8.5 7.9–7.0 4.3–1.2 3.96, 3.93 | " |
| 8 | 1 | 0 | S | H | H | CH₂CH₂OH | OCH₃ | OCH₃ | 136.0~139.5 | 1719 1618 1578 1509 | 10.3, 8.5 7.2, 7.1 4.8–1.2 3.90, 3.93 | DMSO-d₆ |
| 9 | 1 | 0 | S | H | H | CH₂C₆H₅ | OCH₃ | OCH₃ | 126.0~128.0 | 1735 1619 1578 1507 | 8.6, 8.0 7.2, 7.1 4.5–2.6 4.03, 4.00 2.3–1.2 | CDCl₃ |
| 10 | 1 | 0 | S | H | H | CH₂-(imidazolyl) | OCH₃ | OCH₃ | 205.0~207.0 | 1743 1617 1577 1504 | 8.5, 7.5 7.2, 7.1 6.8, 4.6–2.7 2.2–1.2 | DMSO-d₆ |
| 11 | 0 | 0 | S | H | H | CH(CH₃)₂ | OCH₃ | OCH₃ | 245.0 | 1750 1500 1350 | 8.7, 7.5 7.3, 7.1 5.0–1.6 4.0, 1.0 | CDCl₃ |
| 12 | 0 | 0 | S | H | H | CH₂C₆H₅ | OCH₃ | OCH₃ | 160.0~168.0 | 1730 1500 1220 | 8.8, 7.7 7.3, 7.2 5.0–1.6 4.0 | " |
| 13 | 0 | 0 | S | H | H | CH₃ | OCH₃ | OCH₃ | 230.0 | 1740 1500 1250 | 8.6, 7.3 7.2, 5.0–1.6 4.0, 1.3 | " |
| 14 | 0 | 0 | S | H | H | CH₂CH₂SCH₃ | OCH₃ | OCH₃ | 175.0 | 1740 1510 | 8.7, 7.8 7.2, 7.1 5.0–1.6 4.0, 2.0 | " |
| 15 | 1 | 0 | O | H | H | CH(CH₃)₂ | OCH₃ | OCH₃ | 220.0~220.8 | 1766 1704 1622 | 8.7, 7.3 7.1, 6.2 4.3–0.8 | " |

TABLE 5-continued (I)

| | | | Formula (I) | | | | | M.P. | IR(KBr) | NMR(δ) | |
|---|---|---|---|---|---|---|---|---|---|---|---|
| No. | m | n | Z | R¹ | R² | R³ | R⁷ | R⁸ | (°C.) | (cm⁻¹) | (ppm) | Solvent |
| 16 | 1 | 0 | O | H | H | CH₂C₆H₅ | OCH₃ | OCH₃ | 199.0~200.2 | 1577, 1509, 1767, 1706, 1616, 1508 | 4.03, 4.00; 8.6, 7.3; 7.0, 5.7; 2.7-4.4; 4.02, 3.98; 2.0-1.2 | " |
| 17 | 1 | 0 | O | H | H | CH₂C₆H₅—OCH₂C₆H₅—P | OCH₃ | OCH₃ | 159.0~161.0 | 1765, 1710, 1615, 1578, 1505 | 8.6, 7.4-6.8; 5.8, 5.0; 4.4-2.7; 4.01, 3.95; 2.1-1.2 | " |
| 18 | 1 | 0 | O | H | H | CH₂CH(CH₃)₂ | OCH₃ | OCH₃ | 213.5~215.5 | 1760, 1702, 1614, 1580, 1508 | 8.7, 7.3; 7.1, 6.4; 4.3-2.8; 4.03, 4.00; 2.3-0.8 | " |
| 19 | 1 | 0 | O | H | H | CH₂CH₂SCH₃ | OCH₃ | OCH₃ | 222.0~208.0 | 1760, 1708, 1614, 1578, 1508 | 8.7, 7.3; 7.1, 6.3; 4.3-2.6; 4.03, 4.00; 2.3-1.4 | " |
| 20 | 1 | 0 | O | H | H | H | OCH₃ | OCH₃ | 218.0 | 1760, 1700, 1480, 1420 | 8.6, 7.6; 7.2, 7.1; 4.5-1.6; 4.0 | " |
| 21 | 0 | 0 | O | H | H | CH(CH₃)₂ | OCH₃ | OCH₃ | 135.0~137.0 | 1770, 1710, 1500, 1430 | 8.8, 7.3; 7.2, 5.5; 4.6-1.6; 4.0, 1.0 | " |
| 22 | 0 | 0 | O | H | H | —CH₂CH₂SCH₃ | OCH₃ | OCH₃ | 105.0~108.0 | 1770, 1710, 1500, 1420 | 8.5, 7.2; 7.1, 6.3; 4.2-1.6; 3.9, 2.0 | " |
| 23 | 0 | 0 | O | H | H | —CH₂C₆H₅ | OCH₃ | OCH₃ | 147.0~148.0 | 1780, 1700, 1500, 1430 | 8.7, 7.3; 7.1, 5.6; 4.4-1.6; 4.0 | " |
| 24 | 1 | 1 | O | H | —CH₂CH₂CH₂— | | OCH₃ | OCH₃ | 168.0~169.0 | 1760, 1700, 1500, 1430 | 8.7, 8.3; 8.1, 4.4-1.5; 4.0 | " |
| 25 | 1 | 0 | O | CH₃ | —CH₂CH₂CH₂— | | OCH₃ | OCH₃ | 194.0~197.0 | 1760, 1700, 1500 | 8.7, 8.3; 8.1, 4.4-1.0; 4.0, 1.4 | " |
| 26 | 1 | 1 | S | H | H | CH(CH₃)₂ | OCH₃ | OCH₃ | 211.0~213.0 | 1740, 1500, 1435 | 8.7, 7.8; 7.3, 7.2; 4.4-1.4; 1.0 | " |
| 27 | 1 | 1 | O | H | H | CH(CH₃)₂ | OCH₃ | OCH₃ | 276.0~279.0 | 1765, 1705, 1500, 1435 | 8.6, 7.3, 7.1; 7.0, 4.4-1.4; 4.0; 1.0 | " |
| 28 | 1 | 0 | O | CH₃ | H | CH(CH₃)₂ | OCH₃ | OCH₃ | 217.0~218.0 | 1770, 1700, 1505, 1425 | 8.7, 7.3; 7.1, 6.2; 4.4-1.4; 4.0, 1.5, 1.0 | " |

The acute toxicity and cardiotonic activity of the selected compounds (I) were tested as follows:

(I) Acute toxicity

Compounds (I) exhibit a low toxicity. For example, when the compound described in Example 1 hereinbefore (Compound 1) was orally given to mice at a dose of up to 300 mg/kg, all animals (three) survived one week after administration.

(II) Cardiotonic activity (1) Testing method

Mongrel dogs (adults; female and male) having a body weight of 8-15 kg were anaesthesized by injection (iv.) of sodium pentobarbital (30 mg/kg). Under artificial respiration, a catheter-type pressure transducer was inserted into the left ventricle to measure the inner pressure. A catheter was inserted into the femoral artery to measure the peripheral blood pressure. The cardiac contractile force was measured by referring to the maximum value of the primary differential of the blood pressure in the left ventricle (dp/dt max.). The heart rate was measured by introducing ECG wave (second induction) into a tachometer. During the measuring, anaesthesia was continued by means of inhalation of halothane and $N_2O$ gas. Simultaneously with the anaesthesia, a muscle relaxant (panchronium bromide) was continuously injected into the vein at the left paw at a rate of 0.1 mg/kg/hour to stabilise the anaesthesia for a long period of time.

Each test compound was dissolved in PEG-400 and administered into the vein at the right paw at a dose of 0.3 mg/kg. For a period of 60 minutes the maximum rate of change of the cardiac contractile force and heart rate, as well as the average blood pressure, were measured and compared with the corresponding values measured before administration. The duration of the change of the cardiac contractile force was also measured.

(2) The results are shown in Table 6.

TABLE 6

| Compound No. | Animals | Dose (iv) (mg/kg) | dp/dt max % change | Heart rate (max.) % change | Blood pressure (max) % change | Duration (min.) |
|---|---|---|---|---|---|---|
| 1 | 3 | 0.3 | 65.6 ± 3.4 | 22.3 ± 7.0 | −28.7 ± 6.4 | >60 |
| 2 | 3 | 0.3 | 67.8 ± 1.2 | 16.7 ± 5.5 | −20.6 ± 12.6 | >60 |
| 3 | 3 | 0.3 | 37.3 ± 6.0 | 5.8 ± 4.0 | −25.8 ± 7.7 | 15 |
| 4 | 4 | 0.3 | 33.6 ± 5.7 | 8.0 ± 1.2 | −9.4 ± 2.6 | 30 |
| 5 | 3 | 0.3 | 33.8 ± 3.4 | 6.4 ± 3.8 | −23.6 ± 0.9 | 30 |
| 6 | 3 | 0.3 | 46.9 ± 10.6 | 11.8 ± 3.4 | −33.2 ± 5.3 | 30 |
| 7 | 2 | 0.3 | 0.4 ± 0.4 | −1.7 ± 0.9 | −5.3 ± 0.3 | — |
| 8 | 3 | 0.3 | 32.9 ± 6.2 | 3.5 ± 1.8 | −15.3 ± 1.9 | 30 |
| 9 | 3 | 0.3 | 52.9 ± 4.6 | 5.6 ± 0.6 | −27.1 ± 3.5 | 45 |
| 10 | 3 | 0.3 | 8.3 ± 3.4 | −0.8 ± 0.4 | −11.6 ± 4.9 | 15 |
| 11 | 3 | 0.3 | 36.3 ± 8.5 | 6.4 ± 1.1 | −16.5 ± 8.6 | 60 |
| 13 | 3 | 0.3 | 32.7 ± 0.7 | 6.0 ± 1.5 | −13.4 ± 5.1 | 15 |
| 14 | 3 | 0.3 | 41.0 ± 2.8 | 2.6 ± 0.7 | −30.1 ± 6.4 | 30 |
| 15 | 3 | 0.3 | 57.1 ± 13.9 | 9.9 ± 2.0 | −26.3 ± 5.8 | 60 |

| Compound No. | Animals | Dose (iv) (mg/kg) | dp/dt max % change | Heart rate (max.) % change | Blood pressure (max) % change | Duration (min.) |
|---|---|---|---|---|---|---|
| 16 | 3 | 0.3 | 47.9 ± 4.0 | 3.5 ± 0.9 | −21.3 ± 3.4 | 30 |
| 17 | 2 | 0.3 | 2.0 ± 0.3 | −3.1 ± 0.4 | −7.3 ± 2.1 | — |
| 18 | 3 | 0.3 | 22.8 ± 4.0 | 1.8 ± 0.9 | −2.4 ± 1.3 | 30 |
| 19 | 3 | 0.3 | 34.8 ± 6.9 | 11.4 ± 2.0 | −25.2 ± 6.8 | 15 |
| 20 | 3 | 1.0 | 29.6 ± 10.5 | 6.1 ± 2.5 | −14.6 ± 3.6 | 25 |
| 21 | 3 | 0.3 | 39.3 ± 7.8 | 7.3 ± 4.1 | −21.9 ± 11.2 | 30 |
| 22 | 3 | 0.3 | 66.8 ± 16.9 | 6.8 ± 1.8 | −17.0 ± 8.2 | 30 |
| 23 | 3 | 0.3 | 57.3 ± 7.3 | 5.1 ± 2.1 | −11.6 ± 6.1 | 30 |
| 24 | 3 | 0.3 | 63.1 ± 3.4 | 16.1 ± 1.0 | −9.9 ± 5.2 | 45 |
| 25 | 3 | 0.3 | 35.8 ± 2.6 | 8.0 ± 2.6 | 5.1 ± 1.8 | 15 |
| 26 | 3 | 0.3 | 68.7 ± 12.4 | 12.5 ± 3.7 | −23.5 ± 7.1 | >60 |
| 27 | 3 | 0.3 | 87.1 ± 6.9 | 25.6 ± 5.6 | −12.8 ± 3.2 | 45 |
| 28 | 3 | 0.3 | 76.6 ± 9.6 | 13.0 ± 0.3 | −14.4 ± 4.3 | 45 |
| *UK-14275 | 3 | 0.3 | 27.5 ± 11.7 | 1.2 ± 1.2 | 2.2 ± 0.8 | 15 |

*Control

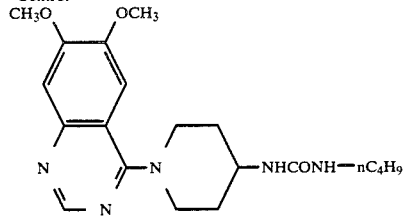

What is claimed is:

1. Quinazoline derivatives and pharmaceutically acceptable acid addition salts thereof having the general formula

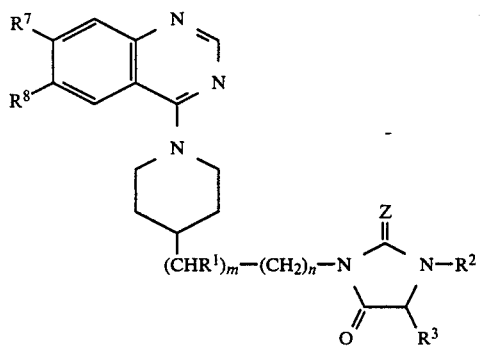 (I)

Wherein $R^1$ and $R^2$ are each selected from the group consisting of hydrogen and a $C_1$ to $C_6$ alkyl group;

$R^3$ is selected from the group consisting of a $C_1$ to $C_6$ alkyl group and $-(CH_2)_p-Q$; or $R^2$ and $R^3$ may together form the group $-CH_2CH_2CH_2-$;

Q is selected from the group consisting of hydroxy, an alkylthio group having 1 to 5 carbon atoms, imidazolyl, phenyl, and substituted phenyl wherein the substituent is selected from the group consisting of hydroxy, methoxy, ethoxy and benzyloxy;

p represents an integer of from 1 to 5;

$R^7$ and $R^8$ each represent a $C_1$ to $C_5$ alkoxy group;

Z represents a member of the group consisting of oxygen and sulfur atoms;

m represents 0 or 1; and n represents 0 or an integer from 1 to 4.

2. The compound of claim 1 which is 1-(6,7-dimethoxy-quinazolin-4-yl)-4-(5-isopropyl-4-oxo-2-thioxoimidazolidin-3-yl)methyl piperidine or a pharmaceutically acceptable acid addition salt thereof.

3. The compound of claim 1 which is 1-(6,7-dimethox yquinazolin-4-4-yl)-4-(5-isopropyl-1-methyl-4-oxo-2-thioxoimidazolidin-3-yl)methylpiperidine or a pharmaceutically acceptable acid addition salt.

4. The compound of claim 1 which is 1-(6,7-dimethoxyquinazolin-4-yl)-4-(5-isopropyl-4-oxo-2-thioxoimidazolidin-3-yl)piperidine or a pharmaceutically acceptable acid addition salt thereof. thereof.

5. The compound of claim 1 which is 1-(6,7-dimethoxyquinazolin-4-yl)-4-(5-isopropyl-2,4-dioxoimidazolidin-3-yl)methylpiperidine or a pharmaceutically acceptable acid addition salt thereof.

6. The compound of claim 1 which is 1-(6,7-dimethoxyquinazolin-4-yl)-4-{2-(5-isopropyl-2-thio-4-oxoimidazolidin-3-yl)ethyl}piperidine or a pharmaceutically acceptable acid addition salt thereof.

7. A pharmaceutical composition which has a cardiotonic activity and which comprises an effective amount of a compound of claim 1, as an active ingredient and a physiologically acceptable carrier, excipient or adjuvant.

* * * * *